(12) United States Patent
Randolph et al.

(10) Patent No.: US 11,672,725 B2
(45) Date of Patent: Jun. 13, 2023

(54) SYSTEM AND METHOD UTILIZING VACUUM FOR PROMOTING THE HEALING OF SPRAINS

(71) Applicant: KCI Licensing, Inc., San Antonio, TX (US)

(72) Inventors: Larry Tab Randolph, San Antonio, TX (US); Christopher Brian Locke, Bournemouth (GB); James Seddon, Ferndown (GB); T. Blane Sanders, San Antonio, TX (US); Richard Marvin Kazala, Jr., San Antonio, TX (US); Lillian Ramos, San Antonio, TX (US); Carrie Ann Kauffman, San Antonio, TX (US); Marisa Schmidt, San Antonio, TX (US); Jessica Ann Rivas-Bosquez, Pasadena, CA (US); Chester Edlund, San Antonio, TX (US)

( * ) Notice: Subject to any disclaimer, the term of this patent is extended or adjusted under 35 U.S.C. 154(b) by 1183 days.

(21) Appl. No.: 16/251,414

(22) Filed: Jan. 18, 2019

(65) Prior Publication Data
US 2019/0151188 A1 May 23, 2019

Related U.S. Application Data

(63) Continuation of application No. 14/204,878, filed on Mar. 11, 2014, now Pat. No. 10,219,973.
(Continued)

(51) Int. Cl.
*A61H 9/00* (2006.01)
*A61M 1/08* (2006.01)
*A61M 1/00* (2006.01)

(52) U.S. Cl.
CPC ............ *A61H 9/00* (2013.01); *A61H 9/0057* (2013.01); *A61H 9/0092* (2013.01);
(Continued)

(58) Field of Classification Search
CPC ... A61H 9/0057; A61H 9/005; A61M 1/0088; A61M 1/009; A61F 13/00068
See application file for complete search history.

(56) References Cited

U.S. PATENT DOCUMENTS

| 1,355,846 | A | 10/1920 | Rannells |
| 2,547,758 | A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Michael J Tsai

(57) ABSTRACT

A system and apparatus for promoting perfusion at a tissue site containing a sprain by applying a vacuum to intact skin extending over or surrounding the tissue site. The system and apparatus comprise a manifold formed from a porous material and configured to be disposed proximate the intact skin for distributing vacuum to the intact skin, and a sleeve adapted to cover the manifold and form a chamber containing the manifold to seal the manifold within the chamber between the sleeve and the intact skin. The system and apparatus further comprise a fluid coupling member adapted to deliver vacuum to the manifold for distribution to the intact skin. A method for applying vacuum to the intact skin of a tissue site is also disclosed and described herein.

22 Claims, 7 Drawing Sheets

Related U.S. Application Data

(60) Provisional application No. 61/778,042, filed on Mar. 12, 2013.

(52) U.S. Cl.
CPC .. *A61H 2201/164* (2013.01); *A61H 2201/165* (2013.01); *A61H 2201/1635* (2013.01); *A61H 2201/1697* (2013.01); *A61H 2205/06* (2013.01); *A61H 2205/065* (2013.01); *A61H 2205/102* (2013.01); *A61H 2205/106* (2013.01); *A61H 2205/12* (2013.01); *A61H 2209/00* (2013.01); *A61M 1/08* (2013.01); *A61M 1/915* (2021.05); *A61M 1/917* (2021.05)

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 5,749,100 | A | 5/1998 | Rosenberg |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,074,200 | B1 | 7/2006 | Lewis |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,663,198 | B2 | 3/2014 | Buan et al. |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2002/0169399 | A1* | 11/2002 | Rastegar .............. A61H 31/006 601/9 |
| 2004/0024322 | A1* | 2/2004 | Caspers .................. A61F 2/80 600/481 |
| 2005/0027218 | A1* | 2/2005 | Filtvedt ................. A61H 9/005 601/9 |
| 2005/0203452 | A1 | 9/2005 | Weston et al. |
| 2005/0261615 | A1* | 11/2005 | Weston .................. A61M 1/84 602/13 |
| 2006/0287621 | A1* | 12/2006 | Atkinson ............. A61H 9/0078 601/151 |
| 2007/0167884 | A1* | 7/2007 | Mangrum .............. A61H 9/005 601/6 |
| 2007/0218101 | A1 | 9/2007 | Johnson et al. |

(56) References Cited

U.S. PATENT DOCUMENTS

| | | | |
|---|---|---|---|
| 2007/0219585 A1* | 9/2007 | Cornet | A61H 9/005 606/221 |
| 2008/0208088 A1* | 8/2008 | Cazzini | A61M 1/75 602/13 |
| 2009/0177184 A1* | 7/2009 | Christensen | A61H 9/0057 604/113 |
| 2009/0299257 A1 | 12/2009 | Long et al. | |
| 2011/0295168 A1 | 12/2011 | Mangrum et al. | |
| 2012/0046626 A1 | 2/2012 | Sanders et al. | |
| 2012/0203144 A1 | 8/2012 | Collins | |
| 2012/0209226 A1 | 8/2012 | Simmons et al. | |
| 2013/0123722 A1 | 5/2013 | Pratt et al. | |
| 2014/0163491 A1 | 6/2014 | Schuessler et al. | |
| 2015/0080788 A1 | 3/2015 | Blott et al. | |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| DE | 102008009455 A1 | 8/2009 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| EP | 2319550 A1 | 5/2011 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | WO-0180790 A1 * | 11/2001 | A61F 7/10 |
| WO | 2009158128 A2 | 12/2009 | |
| WO | 2009158130 A1 | 12/2009 | |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634 639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

(56) References Cited

OTHER PUBLICATIONS

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

Extended European Search Report for Corresponding Application No. 201838091, dated Oct. 26, 2020.

European Examination Report for Corresponding Application No. 147228183, dated Aug. 23, 2019.

\* cited by examiner

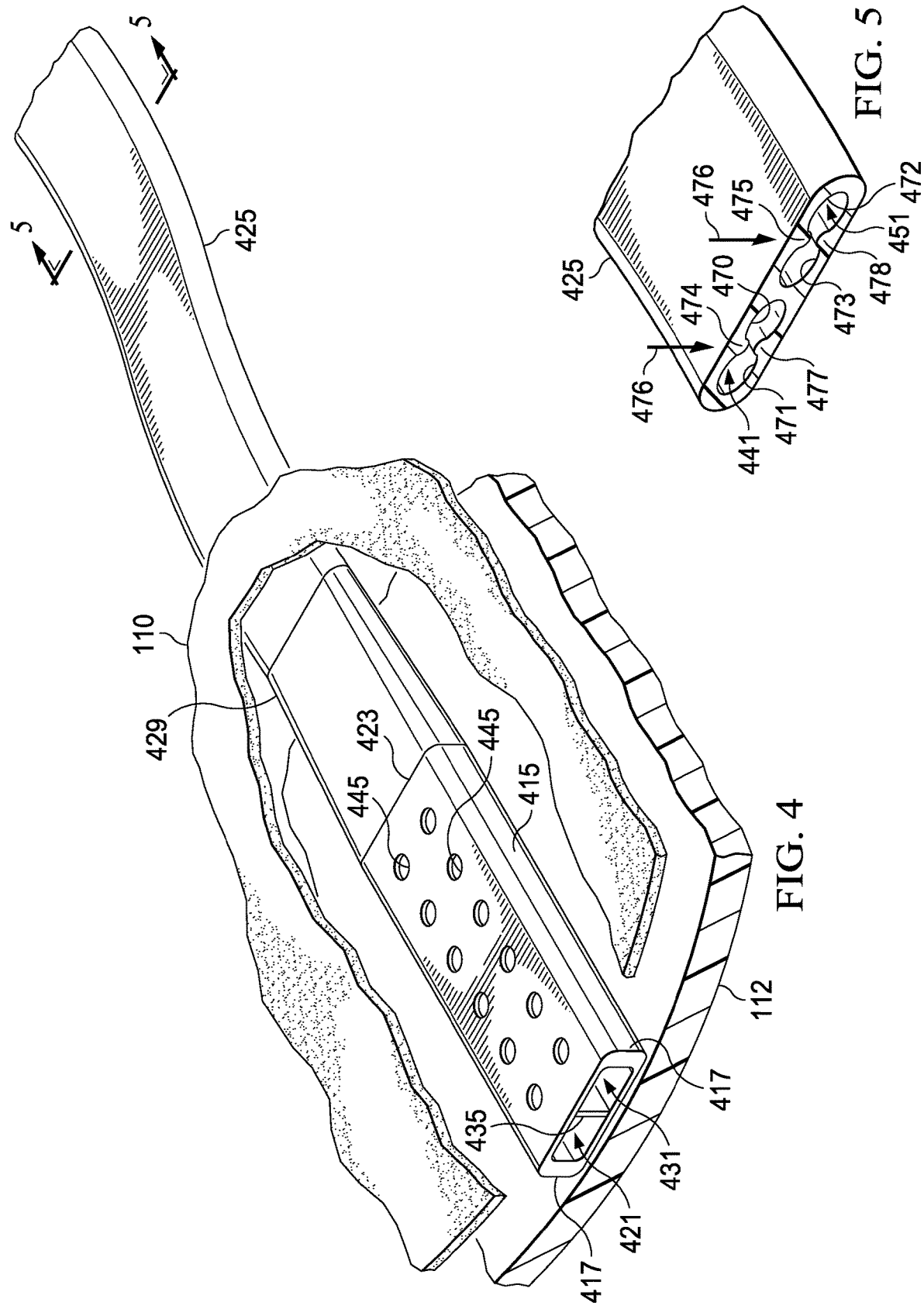

SYSTEM AND METHOD UTILIZING VACUUM FOR PROMOTING THE HEALING OF SPRAINS

RELATED APPLICATION

The present invention is a continuation of U.S. patent application Ser. No. 14/204,878, entitled "SYSTEM AND METHOD UTILIZING VACUUM FOR PROMOTING THE HEALING OF SPRAINS," filed Mar. 11, 2014, which claims the benefit, under 35 USC § 119(e), of the filing of U.S. Provisional Patent Application Ser. No. 61/778,042, entitled "SYSTEM AND METHOD UTILIZING VACUUM FOR PROMOTING THE HEALING OF SPRAINS," filed Mar. 12, 2013, which is incorporated herein by reference for all purposes.

TECHNICAL FIELD

The present disclosure relates generally to medical treatment systems for treating tissue sites that include sprains and strains to subcutaneous tissue such as, for example, a ligament or a muscle. More particularly, but not by way of limitation, the present disclosure relates to a system for applying vacuum to intact skin extending over or surrounding a tissue site that has been sprained to stimulate blood flow by perfusion thereby reducing edema and promoting the healing of the sprain injury at the tissue site.

BACKGROUND

A sprain is an injury resulting from the wrenching or twisting of a ligament or muscle of a joint, such as a knee or ankle, characterized by clinical symptoms including swelling, bruising or contusions, pain, and disablement of the joint. A sprain may further be characterized by edema which is an abnormal accumulation of fluid in cells, tissues, or cavities of the body resulting in swelling. Strains are sprains caused by exertion or an acute trauma event. These trauma events can include, for example, an abnormal muscle contraction, a high amount of specifically applied tension, or forced stretching of the muscle of the ligament. These injuries can be extremely debilitating, especially to professional and amateur athletes who can no longer participate in physical activities. In addition, the affected area, most commonly extremities such as the foot, ankle and knee, suffer from reduced range of motion.

Acute inflammation is a response to any type of trauma including trauma events causing a sprain or strain wherein the inflammation protects the tissue and removes any damaged material or tissue from the body. Enzymatic signaling agents including histamine, serotonin, bradykinin, and prostaglandin are normally released as part of the inflammatory process. These agents increase capillary membrane permeability in order to enhance the inflammatory process, but also result in edema from fluid accumulation during the interstitial phase. The signaling agents, therefore, cause the primary symptoms of inflammation: swelling, heat, redness and pain. This initial phase of inflammation can start after one or two days and end after three or four days. In some cases, the damage to the ligament can be even more severe. For example, high ankle sprains involve injury to the ligament above the ankle that joins together the tibia and fibula, or syndesmotic ligament. Regardless of the type of strain or sprain, a single injury has been shown to place the affected extremity at significantly greater risk of re-injury even after the first injury has healed.

Sprains and strains affect a significant number of individuals every year. In the US alone, 14 million patients were admitted into outpatient care for sprains or strains of the foot and ankle alone. Another 20 million patients were admitted for sprains or strains of the knee. Many of these sprains and strains can be extremely debilitating, limiting mobility and causing pain for a long period of time. While these injuries have an impact on the average individual's activity levels, their impact is especially profound for athletes. Athletes, both professional and amateur, are severally limited by these injuries and often reinjure themselves because they return to the physical activity too soon ignoring the long time period necessary for complete healing of the injury. In the US alone, the costs charged to Medicare for outpatient strains or sprains were $390M in 2011, while the costs charged to private insurance were $1.2B in 2011.

SUMMARY OF ILLUSTRATIVE EMBODIMENTS

According to an illustrative embodiment, a system for applying vacuum to intact skin extending over or surrounding a tissue site injured by a sprain is effective to stimulate blood flow by perfusion thereby reducing edema and promoting the healing of the sprain at the tissue site. The application of vacuum to the intact skin stimulates the flow of blood by decompressing the intact skin over the tissue site which causes perfusion in the subcutaneous vascular system of the tissue site where the sprain occurs. The decompression therapy and perfusion enhances circulation and flushes out fluid in the cells to reduce edema and promote healing of the sprain more quickly than the current standard of care.

An exemplary embodiment of an apparatus for promoting perfusion at a tissue site containing a sprain by applying vacuum to intact skin extending over or surrounding the tissue site comprises a manifold formed from a porous material having an open cell structure and configured to be disposed proximate the intact skin for distributing vacuum to the intact skin, and a sleeve formed from a semi-permeable material adapted to cover the manifold and form a chamber containing the manifold to seal the manifold within the chamber between the sleeve and the intact skin. The apparatus may further comprises a fluid coupling member adapted to receive vacuum from a vacuum source which is fluidly coupled to the manifold.

The manifold may also be adapted to wick fluid away from the intact skin into the fluid coupling member. The sleeve may be an elastomeric material adapted to seal the manifold sufficiently within the chamber to attain a desired vacuum. The apparatus may further comprise a comfort layer disposed in the chamber between the intact skin and the manifold. The fluid coupling member may comprise a housing defining an interior space adapted to be in fluid communication with the manifold.

An exemplary embodiment of a system for promoting perfusion at a tissue site containing a sprain by applying vacuum to intact skin extending over or surrounding the tissue site comprises a vacuum source for providing vacuum to the intact skin. The system further comprises a manifold formed from a porous material having an open cell structure and configured to be disposed proximate the intact skin for distributing vacuum to the intact skin, and a sleeve formed from a semi-permeable material adapted to cover the manifold and form a chamber containing the manifold to seal the manifold within the chamber between the sleeve and the intact skin. The system may further comprise a fluid coupling member adapted to receive vacuum from the vacuum source which is fluidly coupled to the manifold to deliver vacuum for distribution to the intact skin.

An exemplary embodiment of a method for applying vacuum to the intact skin of a tissue site is also disclosed. The method comprises disposing a manifold proximate the intact skin of the tissue site wherein the manifold is formed from a porous material, enclosing the manifold with a sleeve formed from a semi-permeable material that seals the manifold within a chamber between the sleeve and the intact skin, and fluidly coupling the manifold to a vacuum source so that the manifold distributes vacuum to the intact skin of the tissue site.

And another exemplary embodiment of applying vacuum to the intact skin for promoting perfusion at a tissue site containing a sprain comprises disposing a dressing proximate the intact skin extending over the tissue site for distributing vacuum to the intact skin. The dressing comprises a manifold formed from a porous material having flow channels and configured to be disposed proximate the intact skin for distributing vacuum to the intact skin, and a sleeve formed from a semi-permeable material and adapted to cover the manifold and form a chamber containing the manifold to seal the manifold within the chamber between the sleeve and the intact skin.

Other aspects, features, and advantages of the illustrative embodiments will become apparent with reference to the drawings and detailed description that follow.

BRIEF DESCRIPTION OF THE DRAWINGS

FIG. 4 is an exploded, perspective, sectional view of a portion of the sleeve and manifold of FIG. 1 and a vacuum delivery manifold according to another illustrative embodiment;

FIG. 5 is cross-sectional view of the conduit of FIG. 4 taken on the line 5-5;

DETAILED DESCRIPTION OF ILLUSTRATIVE EMBODIMENTS

New and useful systems, methods, and apparatuses for treating tissue sites that include sprains and strains to subcutaneous tissue such as, for example, a ligament or a muscle. are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

The exemplary embodiments may also be described herein in the context of reduced-pressure therapy applications or vacuum therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure or vacuum therapy. However, as should be recognized by those skilled in the art, this frame of reference is merely a descriptive expedient rather than a strict prescription.

Figure 1:
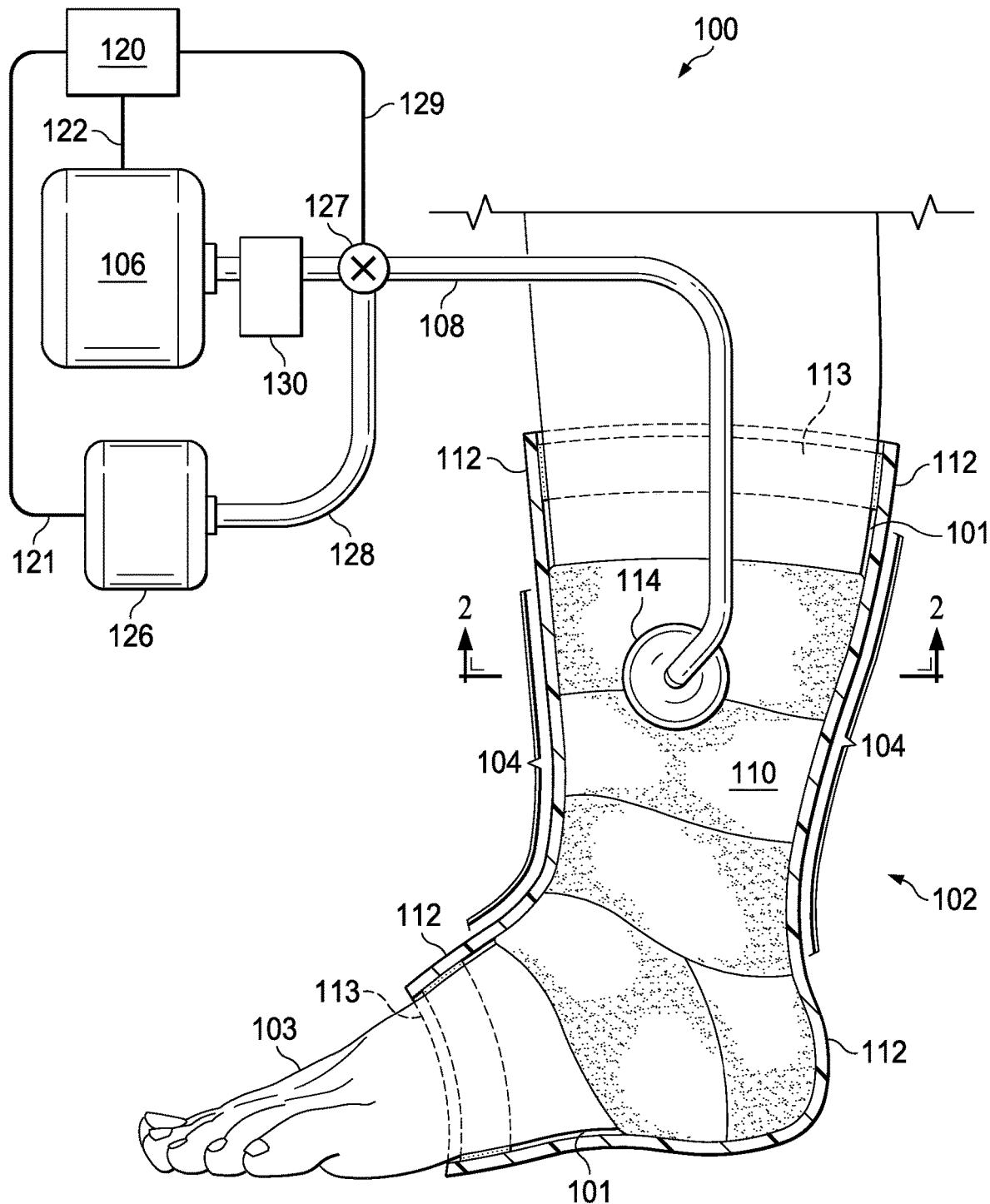
FIG. 1 is a side view of a system comprising a first exemplary embodiment of a dressing including a sleeve and a manifold for applying vacuum to a tissue site on the ankle portion of a foot according to an illustrative embodiment.
Figure 2:
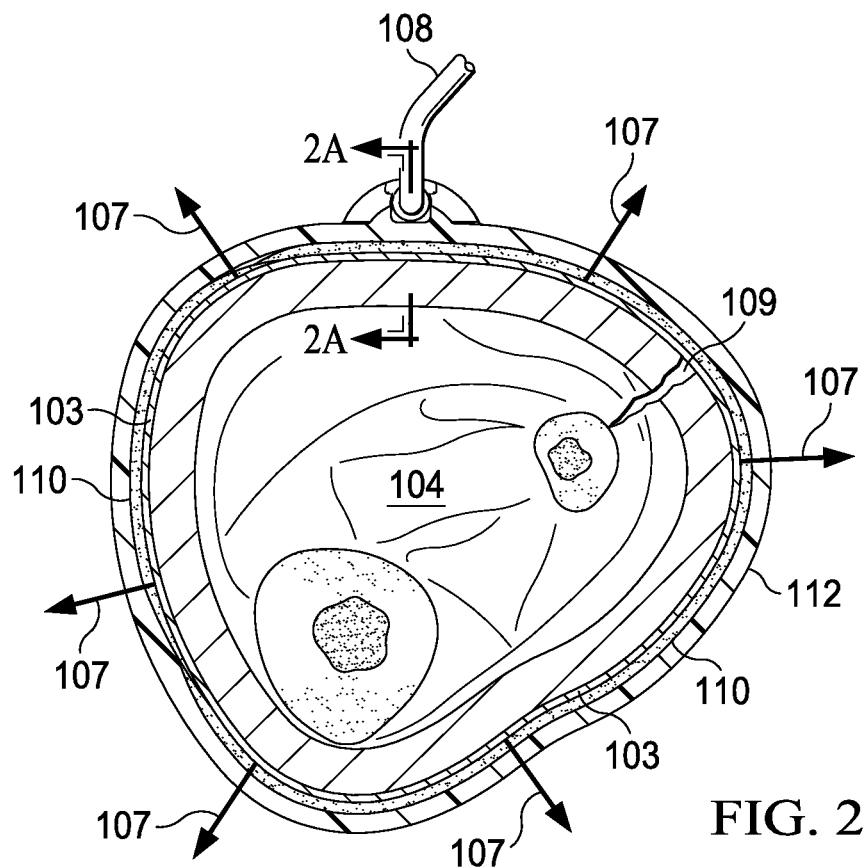
FIG. 2 is a cross-sectional view of the dressing also including a connector disposed on the sleeve and that portion of the tissue site above the ankle of FIG. 1 taken along the line 2-2.

Referring to FIGS. 1 and 2, an exemplary embodiment of a therapy system 100 is shown and comprises a dressing 102 for applying vacuum to intact skin over or surrounding a tissue site such as, for example, tissue site 104 above the ankle portion of a foot 103, a vacuum source 106 for providing the vacuum, and a conduit 108 fluidly coupling the vacuum source 106 to the dressing 102. In this embodiment, the dressing 102 forms a chamber 101 with the intact skin around the tissue site 104. The dressing 102 extends around and seals the ankle portion of the foot 103 that has been sprained. Other exemplary embodiments of the dressing 102 may include similar dressings for the treatment of ligaments or muscles associated with any other joint such as, for example, a knee, ankle, wrist, or elbow joint. Yet other exemplary embodiments may cover only the intact skin that extends over a portion of the tissue site 104 that contains the sprain without being wrapped around the limb. For example, if the sprain is close to the epidermal tissue, such embodiments may be applied more locally to that portion of the intact skin that is adjacent the sprain.

The term "tissue site" in this context broadly refers to the location of any tissue associated with a joint including but not limited to, bone tissue, adipose tissue, muscle tissue, neural tissue, dermal tissue, vascular tissue, connective tissue, cartilage, tendons, or ligaments. As described above, sprains are injuries to a ligament or a muscle at the tissue site which may cause further injury to the other tissue at the tissue site. However, in this context, such injuries are subcutaneous within the tissue site as opposed to an open wound or defect on the epidermis and/or dermis where the skin may remain substantially intact with no open wounds or defects. Thus, the dressing 102 is adapted to apply vacuum to the intact skin such as, for example, the epidermis 103 extending over or surrounding the tissue site 104. The dressing 102 forms a space such as, for example, the chamber 101, between the epidermis 103 and a portion of the dressing 102 that functions like a decompression chamber to pull the skin outwardly or distally as illustrated by arrows 107 rather than compressing the tissue site for a sustained period of time. It is to be understood, that the intact skin may include an open wound such as, for example, an incision 109 resulting from surgery to repair a fractured bone associated with the sprain or strain.

The therapy system 100 may further comprise a regulator or controller 120 that may be electrically coupled to the vacuum source 106 by electrical coupling 122 to control the airflow being delivered by the vacuum source 106 to the dressing 102 to achieve the desired vacuum therapy. The therapy system 100 may also include a thermal control system 126 fluidly coupled by a conduit 128 to the conduit 108 through a valve 127. The valve 127 is electrically coupled to the controller 120 by an electrical coupling 129. The thermal control system 126 is electrically coupled by an electrical coupling 121 to the controller 120 to regulate the temperature of the air being delivered to the dressing 102 in order to achieve the desired thermal therapy in conjunction with the desired vacuum therapy. The controller 120 may be programmed to motivate the valve 127 to deliver negative and positive pressure alternately or simultaneously to the dressing 102 through the conduit 108.

The therapy system 100 may also include a fluid container, such as a container 130, fluidly coupled to the vacuum source 106 and the dressing 102 via the valve 127. The container 130 is representative of a container, canister, pouch, or other storage component that can be used to collect and manage fluids withdrawn from the chamber 101 such as, for example, perspiration from the epidermis 103 surrounding the tissue site 104 or exudates from the incision 109. In many environments, a rigid container may be preferred or required for collecting, storing, and disposing of fluids. In other environments, fluids may be properly disposed of without rigid container storage by using a re-usable container that can reduce waste and costs associated with vacuum therapy.

In general, components of the therapy system 100 may be coupled directly or indirectly. Components may be fluidly coupled to each other to provide a path for transferring fluids (for example, liquid and/or gas) between the components. In some embodiments, components may be fluidly coupled with a tube, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

The fluid mechanics of using a vacuum source, such as the vacuum source 106, to reduce the pressure within another component or at another location fluidly connected by a conduit or tube, such as within a sealed therapeutic environment created by the dressing 102, can be mathematically complex. However, the basic principles of fluid mechanics applicable to vacuum therapy are generally well-known to those skilled in the art, and the process of reducing pressure may be described illustratively herein as "delivering," "distributing," or "generating" reduced pressure or vacuum.

In general, exudates and other fluids flow toward lower pressure along a fluid path. Thus, in the context of vacuum therapy, the term "downstream" typically implies something in a fluid path relatively closer to a vacuum source, and conversely, the term "upstream" implies something relatively further away from a vacuum source. Similarly, it may be convenient to describe certain features in terms of fluid "inlet" or "outlet" in such a frame of reference. This orientation is generally presumed for purposes of describing various features and components of vacuum therapy systems herein. However, the fluid path may also be reversed in some applications, such as by substituting a positive-pressure source, and this descriptive convention should not be construed as a limiting convention.

"Reduced pressure" and "vacuum" generally refer to a pressure less than a local ambient pressure, such as the ambient pressure in a local environment external to a sealed therapeutic environment provided by the dressing 102. In many cases, the local ambient pressure may also be the atmospheric pressure in a patient's vicinity. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

A vacuum source, such as the vacuum source 106, may be a reservoir of air at a reduced pressure, or may be a manual or electrically-powered device that can reduce the pressure in a sealed volume, such as a vacuum pump, a suction pump, a wall suction port available at many healthcare facilities, or a micro-pump, for example. The vacuum source may be housed within or used in conjunction with other components, such as sensors, processing units, alarm indicators, memory, databases, software, display devices, or user interfaces that further facilitate vacuum therapy. While the amount and nature of vacuum applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

In other exemplary embodiments, a thermal control system, such as the thermal control system 126, may include a positive-pressure pump to provide a source of temperature-controlled airflow to the sealed therapeutic environment provided by the dressing 102. The controller 120 may be used to increase or decrease the temperature of the airflow provided by the thermal control system 126 alternatively with the vacuum provided by the vacuum source 106. The thermal control system 126 may be used in conjunction with other components of the controller 120 such as sensors, processing units, alarm indicators, memory, databases, software, display devices, or user interfaces that further facilitate instillation therapy. In other exemplary embodiments, the controller 120 may be operable to provide vacuum and thermal control simultaneously or in an alternating cycle.

The dressing 102 comprises a manifold 110 adapted to contact the intact skin surrounding the tissue site 104, a sleeve 112 enclosing the manifold 110 within the chamber 101 proximate the intact skin to provide an airtight seal, and a fluid coupling member such as, for example, connector 114 fluidly coupling the conduit 108 to the manifold 110 through the sleeve 112. The manifold 110 may be any breathable material that distributes vacuum uniformly over the intact skin of the tissue site 104 when subjected to a vacuum. The manifold 110 may be partially or fully in contact with the intact skin of the tissue site 104. For example, the manifold 110 may contact the intact skin surrounding the tissue site 104, but not the incision 109 at the tissue site 104.

Figure 6A:
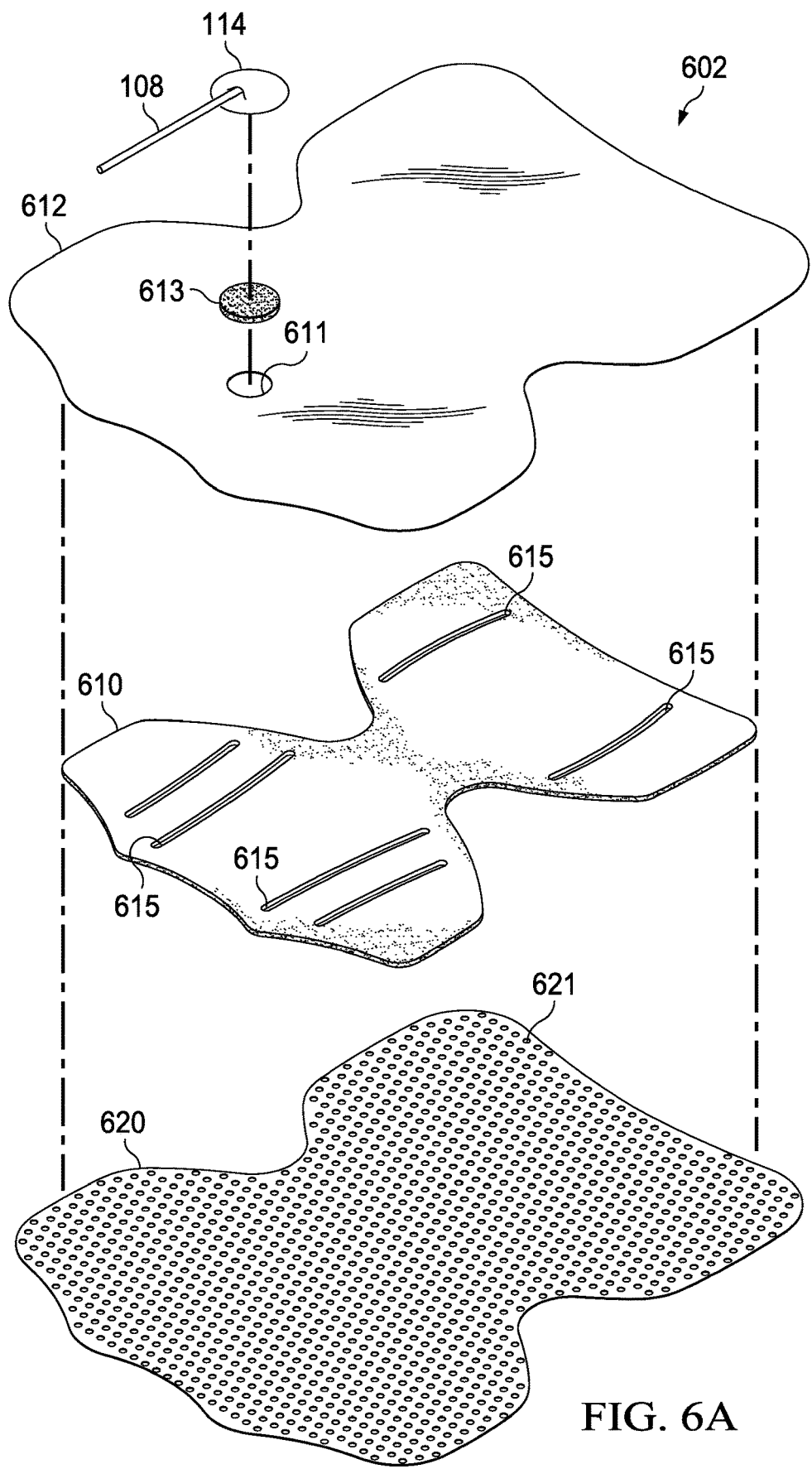
FIG. 6A is an exploded, perspective view of a second exemplary embodiment of a dressing allowing for limb articulation on either side of a joint.

Because the dressing 102 may be positioned on the intact skin for a prolonged period of time, the manifold 110 may possess an antimicrobial property to mitigate the risk of fungal infection and the spread of such infections caused by perspiration and warm temperatures in the chamber 101. The antimicrobial property of the manifold 110 may reduce the effect of VOCs to reduce odors being generated by the dressing 102. The antimicrobial property may be achieved by means of a silver coating that covers the manifold 110 or by a silver additive to the sleeve 112. Using a manifold having an antimicrobial property may be used in conjunction with a charcoal filter (not shown) in connection with providing a vacuum to the dressing 102 via the conduit 108 to further reduce odors generated by the dressing 102. (See, for example, FIG. 6A showing dressing 602 including a charcoal filter 613 positioned between the connector 114 and the manifold 610).

The manifold 110 may take many forms and may come in many sizes, shapes, or thicknesses depending on a variety of factors, such as the type of treatment being provided or the nature and size of the intact skin at the tissue site 104. For example, the size and shape of the manifold 110 may be adapted to the contours of the extremities located at the joint that was sprained. More specifically, the manifold 110 is a first exemplary embodiment of a manifold for distributing vacuum that is formed from open-cell foam tape wrapped circumferentially around the tissue site 104 such as, for example, Kineseo® tape (available from a company bearing the same name and widely known) wrapped to a thickness of greater than approximately 2.0 mm. In a second exemplary embodiment, the manifold 110 may be a single piece of the same foam material described above that is formed in the shape of an open-toe sock and simply pulled over the a tissue site of the affected extremity of the body.

More generally, a manifold is a substance or structure adapted to distribute vacuum to or remove fluids from a tissue site, or both. In some embodiments, though, a manifold may also facilitate delivering fluids to a tissue site, if the fluid path is reversed or a secondary fluid path is provided, for example, when the therapy system 100 is used to supply temperature controlled airflow from the thermal control system 126 to regulate the temperature of the intact skin at the tissue site 104 to promote healing or the evaporation of fluids forming at the tissue site 104. A manifold may include flow channels or pathways that distribute fluids provided to and removed from a tissue site around the manifold. In one illustrative embodiment, the flow channels or pathways may be interconnected to improve distribution of fluids provided to or removed from a tissue site. For example, cellular foam, open-cell foam, porous tissue collections, and other porous material such as gauze or felted mat generally include structural elements arranged to form flow channels. Liquids, gels, and other foams may also include or be cured to include flow channels.

In one illustrative embodiment, the manifold 110 may be a porous foam material having interconnected cells or pores adapted to uniformly (or quasi-uniformly) distribute vacuum to a tissue site. The foam material may be either hydrophobic or hydrophilic depending on the desired therapeutic treatment. In one non-limiting example, the manifold 110 may be an open-cell, reticulated polyurethane foam such as GranuFoam® dressing available from Kinetic Concepts, Inc. of San Antonio, Tex. In another non-limiting example, the manifold 110 may be Dry Web brand dressing material available from Liabletex® having a place of business in San Antonio Tex.

In some embodiments, such as embodiments in which the manifold 110 may be made from a hydrophilic material, the manifold 110 may also wick fluid away from a tissue site while continuing to distribute vacuum to the tissue site. The wicking properties of the manifold 110 may draw fluid away from a tissue site by capillary flow or other wicking mechanisms. An example of a foam material having hydrophilic characteristics is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilic characteristics.

The manifold 110 may also include a comfort layer (not shown) positioned adjacent the intact skin. The comfort layer may be coupled, for example by a heat bond or any other technique, to the manifold 110, or may be an integral component of the manifold 110. The comfort layer may be employed to provide additional comfort for the patient rather than disposing the manifold 110 in direct contact with the intact skin of the patient. The comfort layer may be any material that helps prevent skin irritation without significantly impeding airflow between the manifold 110 and the epidermis 103. The comfort layer may also be any material that wicks liquids such as bodily sweat away from the intact skin to prevent maceration. One exemplary embodiment of the comfort layer is a woven material or a polyester knit textile substrate. Another exemplary embodiment of the comfort layer is a material known as InterDry™ textile material available from Milliken Chemical located in Spartanburg, S.C. The comfort layer may also include antimicrobial substances or lubricants.

The sleeve 112 envelops the manifold 110 within the chamber 101 to seal or enclose both the manifold 110 and the intact skin of the tissue site 104 so that the manifold 110 is positioned within the space between the sleeve 112 and the intact skin of the tissue site 104. Attachment devices 113 may be used at each end of the sleeve 112 to enhance the sealing capability of the sleeve 112 to provide an airtight seal within the chamber 101 occupied by the manifold 110. The sleeve 112 comprises a sealing material that can provide a fluid seal between two environments or components, such as between a therapeutic environment adjacent the intact skin surrounding the tissue site 104 and a local external environment surrounding the sleeve 112. Thus, the sleeve 112 also extends circumferentially around the intact skin of the tissue site 104 essentially forming the chamber 101 enclosing the tissue site 104 to provide a vacuum environment wherein the vacuum is distributed to the intact skin by the manifold 110 through the flow channels of the manifold 110. The sealing material may be, for example, an impermeable or semi-permeable material that provides a seal adequate to maintain a desired vacuum within the chamber 101. For semi-permeable materials, the permeability generally should be low enough to maintain a desired vacuum.

The sealing material may also be formed from an elastomeric material so that sleeve 112 encloses the manifold 110 tightly enough to hold the desired vacuum within the chamber 101. In one non-limiting example, the sleeve 112 may be formed from a pliable, non-breathable silicon material such as Silbione® soft silicon available from Bluestar Silicones located in East Brunswick, N.J. A non-limiting example of a Silbione® soft silicon product found to be useful is Silbione® Product Number RTV 4410 A/B that is sufficiently permeable to maintain a vacuum at the desired levels and sufficiently elastomeric to provide the necessary freedom of movement. The desired vacuum may be, for example, in a pressure range between −100 mm Hg and −150 mm Hg for this type of material covering the manifold 110 by the Kineseo® brand tape described above.

The sleeve 112 may be formed from a sealing material having a high MVTR and may have an acrylic adhesive backing material to seal it over the manifold 110. Sealing material having a high MVTR is used for the sleeve 112 to ensure that the dressing 102 has sufficient evaporative capabilities to allow low levels of potential perspiration to be evaporated from the intact skin surrounding the tissue site 104. The dressing 102 may require a charcoal filter to reduce any odor escaping from between the sleeve 112 and the manifold 110 as a result of perspiration forming between them. The dressing 102 may also require a hydrophobic filter if higher levels of moisture develop as a result of the perspiration an extended wear of the dressing 102.

In one exemplary embodiment, the sleeve 112 is molded as a single component in a generally tubular shape formed from the sealing material described above that is stretched over the affected limb and pulled over the manifold 110 to the tissue site 104. In another exemplary embodiment, the sleeve 112 may be formed from a composite material formed from the sealing material described above and an adhesive material that is wrapped around the manifold 110. In yet another exemplary embodiment, the sleeve 112 and the manifold 110 may be a composite structure formed as a single piece of material shaped to wrap around a limb to cover the tissue site 104.

The attachment devices 113 may be an elastic tape wrapped around each end of the sleeve 112 against the epidermis 103 (not shown) to provide a better airtight seal within the chamber 101 if necessary. In another embodiment, the attachment devices 113 may be disposed between the sleeve 112 and the intact skin of the tissue site 104 as shown for attaching the sealing material of the sleeve 112 to an attachment surface such as, for example, the epidermis 103, a gasket, or another sealing member. The attachment devices 113 may also be an adhesive material that prevents the sleeve 112 from slipping down on the intact skin of the body extremity. The attachment devices 113 may take many forms that provide both sealing and adhesive qualities without irritating or macerating the intact skin. For example, an attachment device may be a medically-acceptable, pressure-sensitive adhesive that extends around the periphery of each end of the sleeve 112 to provide an airtight seal forming the chamber 101 around the tissue site 104 between the intact skin and the sleeve 112. Other exemplary embodiments of the attachment devices 113 may include a double-sided tape, paste, hydrocolloid, hydrogel, silicone gel, organogel, or an acrylic adhesive.

Figure 2A:
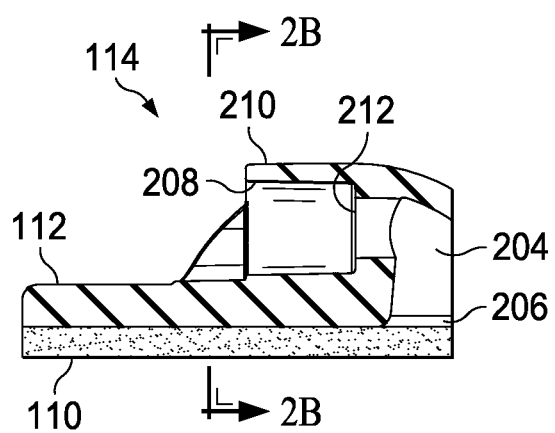
FIG. 2A is an exploded, partial cross-sectional view of the connector disposed on the sleeve as illustrated in FIG. 2.
Figure 2B:
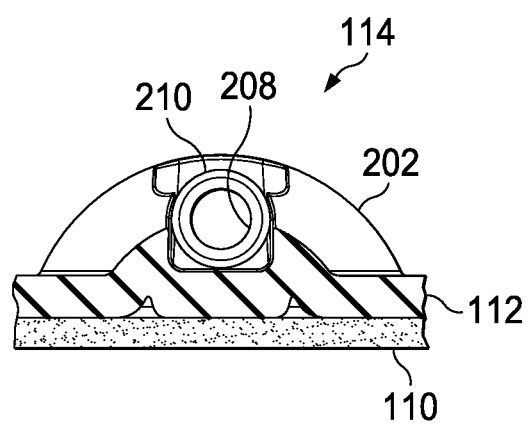
FIG. 2B is an exploded, cross-sectional view of the connector disposed on the sleeve of FIG. 2A taken along the line 2B-2B.

Referring more specifically to FIGS. 2, 2A, and 2B, an aperture is formed on a portion of the sleeve 112 to allow fluid communication between the connector 114 and the manifold 110. As described above, the vacuum source 106 is fluidly coupled to the connector 114 by the conduit 108. The conduit 108 functions to deliver vacuum received through the conduit 108 to the manifold 110. In one exemplary embodiment, the connector 114 includes a housing wall 202 which may have a dome-shaped shape for providing a low-profile and which defines an interior space 204. The interior space 204 has an open portion or interface aperture 206 that is in fluid communication with the manifold 110. The connector 114 further comprises a receptacle 208 formed on the housing wall 202 for receiving and retaining the conduit 108. The receptacle 208 has a first aperture 210 that is sufficiently large to allow the conduit 108 to be coupled with an interference fit and a second aperture 212 that allows fluid to enter while restricting the conduit 108 from entering the interior space 204.

Figure 3:
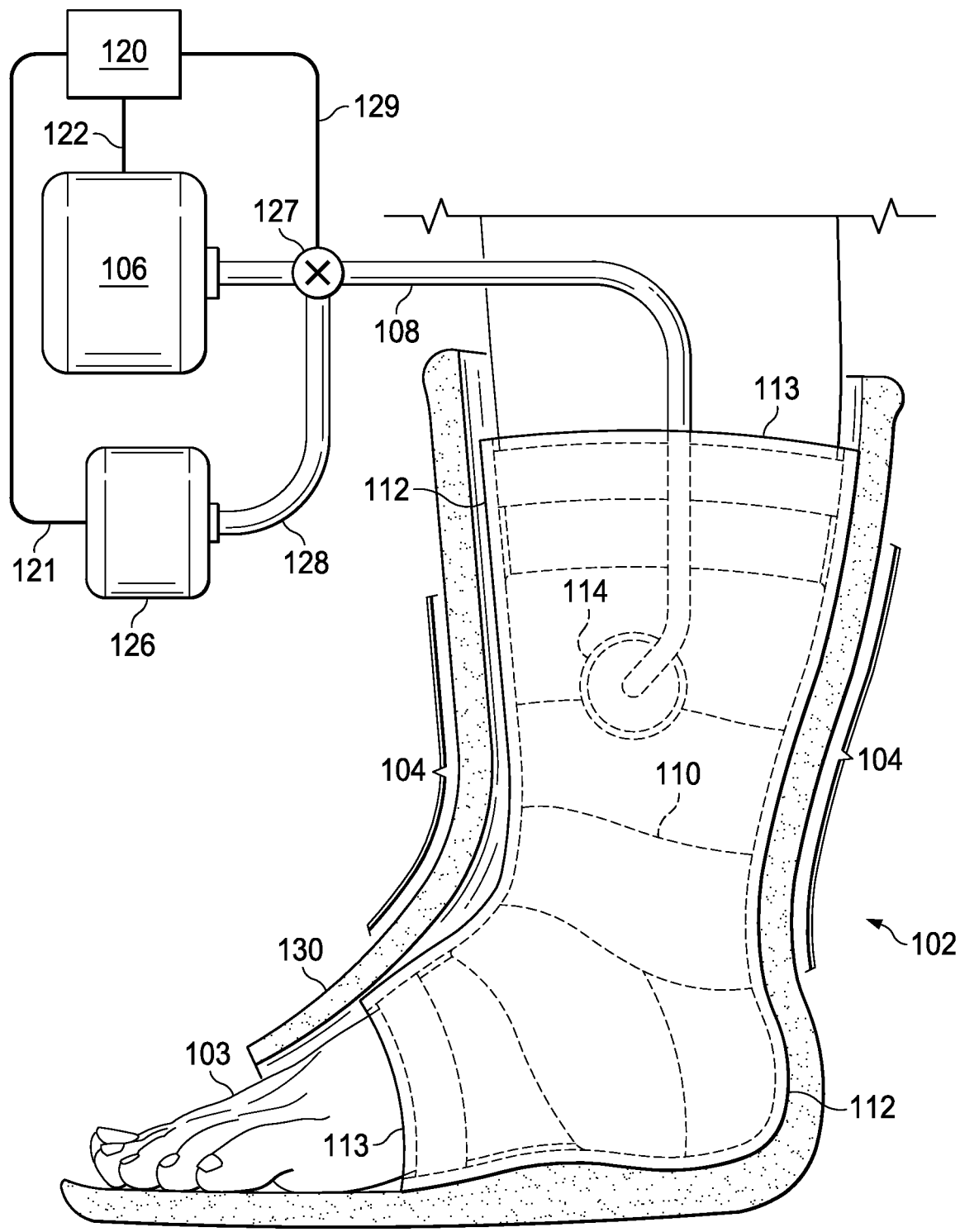
FIG. 3 is a side view of the system and contain the device of FIG. 1 fitted with in a walking boot according to another illustrative embodiment.

Referring to FIG. 3, the therapy system 100 may also include a walking boot or cast 130 enclosing the sleeve 112 to provide support and/or immobilize the joint if necessary. The cast 130 may also be sufficiently rigid to protect the sleeve 112 and manifold 110 from being compressed by contact from the external environment that collapses the manifold 110 preventing the manifold 110 from distributing vacuum to the corresponding portion of the intact skin of the tissue site 104. When a walking boot or cast 130 is utilized, it may be desirable that both the manifold 110 in the sleeve 112 be sufficiently thin to fit comfortably inside the walking boot or cast 130 without diminishing the ability of the manifold 110 to distribute vacuum to the intact skin. Consequently, it is also desirable that the conduit 108 and the connector 114 be sufficiently low-profile and flexible to fit within the walking boot or cast 130 without diminishing their ability to provide vacuum to the manifold 110.

Referring more specifically to FIGS. 4 and 5, a delivery system 411 is another exemplary embodiment that may be used instead of the conduit 108 and the connector 114 to provide a low-profile structure to fit within the walking boot or cast 130. The delivery system 411 includes a delivery manifold 415 having walls 417 surrounding one or more flow passages such as, for example, a first flow passage 421 and a second flow passage 431 separated by a divider 435. The walls 417 are connected at a proximal end 423 to a delivery tube 425 that functions in a similar fashion compared to the conduit 108. The walls 417 may have one or more lumens such as, for example, a first lumen 441 and a second lumen 451. In one exemplary embodiment, the first lumen 441 may be fluidly coupled to the conduit 108 to provide vacuum to the first flow passage 421 of the delivery manifold 415 and the second lumen 451 may be fluidly coupled to the conduit 128 to provide positive pressure to the second flow passage 431 of the delivery manifold 415. The vacuum and positive pressure may each be delivered alternately to both the first lumen 441 and the second lumen 451 as described above, or simultaneously to provide a larger surface area of airflow to the manifold 110.

When the shape of the delivery tube 425 has a circular cross-section similar to the conduit 108 and the cross-sectional shape of the delivery manifold 415 is something other than circular such as, for example, rectangular, a transition region 429 may be provided between the delivery tube 425 and the delivery manifold 415. The delivery manifold 415 may be adhesively connected to the delivery tube 425, connected using other means, such as fusing or insert molding, or alternatively may be integrally connected by co-extrusion. The delivery tube 425 delivers vacuum and/or positive pressure to the delivery manifold 415 for distribution by the manifold 110 proximate to the intact skin of the tissue site 104.

The walls 417 may be made from a flexible material, a rigid material, or a combination of both flexible and rigid materials. For example, a medical grade silicone polymer or other flexible materials may be molded, extruded, or otherwise manufactured to form flexible walls 417. Alternatively, rigid materials including but not limit to metals, polyvinylchloride (PVC), polyurethane, and other rigid polymeric materials may be molded, extruded, or otherwise manufactured to form rigid walls 417.

The walls 417 further include a plurality of apertures 445 through the walls 417 that communicate with the first and second flow passages 421, 431. The apertures 445 allow vacuum and/or positive pressure delivered to the flow passages 421, 431 to be delivered to the manifold 110 for distribution to the intact skin surrounding the tissue site 104. The apertures 445 may be selectively positioned along the length of the delivery manifold 415 to preferentially direct the delivery of vacuum and/or positive pressure more uniformly to the manifold 110. The diameter of the apertures 445 may also vary along the length of the delivery manifold 415 to preferentially direct the delivery of vacuum to the manifold 110 to push excess fluid that accumulates in the tissue site 104 up the blood stream in order to be recycled as described above thereby reducing the swelling and edema.

The delivery tube 425 preferably includes a first lumen 441 having at least one outlet fluidly connected to the first flow passage 421 to deliver vacuum to the first flow passage 421 and through the apertures 445 to the manifold 110. Correspondingly, a second lumen 451 may also be provided that has at least one outlet fluidly coupled to the second flow passage 431 deliver positive pressure to the second flow passage 431 and through the apertures 445 to the manifold 110. The delivery system 411 may include multiple lumens and flow passages for providing vacuum and/or positive pressure to the manifold 110 as required by the therapy treatments. While the end of the walls 417 opposite the end attached to delivery tube 425 may be open as illustrated, it has been found that capping the end of the walls 417 may improve the performance and reliability of the fluid delivery function.

Referring more specifically to FIG. 5, a delivery tube 425 that is functionally analogous to the conduit 108. The delivery tube 425 has an elongated shape having a low profile. The elongated shape of the delivery tube 425 alleviates the pressure points applied to the portions of the foot, ankle, or leg that are adjacent the delivery tube 425. The delivery tube 425 may also have other shapes, such as a circular, elliptical, polygonal, or curved "U" shape depending on the geometry of the tissue site 104. The delivery tube 425 may also be made of any material that is, for example, a flexible, elastic, or compressible material. The flexible, elastic, or compressible material may alleviate the pressure points applied to adjacent portions of the foot, ankle, or leg. Non-limiting examples of material from which the delivery tube 425 may be formed include plastic, nylon, silicon, polyurethane, TPE, or PVC.

The delivery tube 425 includes two lumens 441, 451. In one example, the lumens 441, 451 transfer vacuum to one or both of the flow passages 421, 431 in the delivery manifold 415. The delivery tube 425 may have any number of lumens, including three or more lumens. In addition, one or more of the lumens in the delivery tube 425 may be used to transport fluid, such as liquid or exudate, from a wound to a fluid collection apparatus. In other embodiments, the lumens 441, 451 may have any shape, such as a circular, elliptical, or polygonal shape. The lumen 441 is bound by a first wall 470 and a second wall 471. Similarly, the lumen 441 is bound by a first wall 472 and a second wall 473. The first walls 470, 472 include protrusions 474, 475, respectively. The protrusion 474 prevents the first wall 470 from touching the second wall 471 when a force is applied to the delivery tube 425 in a direction indicated by arrows 476. The protrusion 475 prevents the first wall 472 from touching the second wall 473 when a force is applied to the delivery tube 425 in a direction indicated by arrows 476. In this manner, the protrusions 474, 475 help prevent the lumens 441, 451 from collapsing.

The second walls 471, 473 include protrusions 477, 478, respectively. The protrusion 474 touches protrusion 477 when a force is applied to the delivery tube 425 in a direction indicated by arrows 476 such that the portion of the first wall 470 and the second wall 471 that do not have protrusions 474 and 477 do not touch one another. Similarly, the protrusion 475 touches protrusion 478 when a force is applied to the delivery tube 425 in a direction indicated by arrows 476 such that the portion of the first wall 472 and the second wall 473 that do not have protrusions 475 and 478 do not touch one another. The lumen 441, 451 may be prevented from collapsing in this manner. Thus, the delivery tube 425 provides a low-profile structure that may fit within the walking boot or cast 130 without diminishing its ability to provide a vacuum and/or positive pressure to the manifold 110 because the protrusions prevent the delivery tube 425 from collapsing.

As described above, the manifold 110 may be disposed proximate the intact skin that extends over or around the tissue site 104 so that the chamber 101 envelops the sprain injury at the tissue site 104. The sleeve 112 covers the manifold 110 to seal or enclose the manifold 110 and the intact skin of the tissue site 104 within the chamber 101. Consequently, the sleeve 112 also extends over the intact skin of the tissue site 104 essentially forming the chamber 101 and enclosing the tissue site 104 to provide a vacuum environment wherein the vacuum is distributed to the intact skin by the manifold 110. The dressing 102 provides a sealed therapeutic environment proximate to the intact skin surrounding a tissue site and substantially isolated from the external, ambient environment outside the sleeve 112. Referring back to FIG. 1, the dressing 102 is shown before applying a vacuum to the manifold 110 as illustrated by the open spaces within the chamber 101 at either ends of the dressing 102 between the intact skin and the sleeve 112. When the vacuum source 106 applies a vacuum to the chamber 101, the sleeve 112 collapses slightly against the intact skin surrounding the tissue site 104 until the vacuum removes most of the air from the chamber 101 as shown in FIG. 2. Thus, the sleeve 112 initially collapses against the intact skin surrounding the tissue site 104 and provides a certain amount of stiffening that functions like a splint to stabilize the tissue site 104 and the joint itself as described above.

When the vacuum evacuates most of the air from the chamber 101 so that the sleeve 112 is fully collapsed and the manifold 110 is compressed, the vacuum then begins to pull the intact skin radially outwardly as described above and shown in FIG. 2 because the flow channels within the manifold 110 to not collapse under the vacuum. Instead, the flow channels of the manifold 110 remain open to apply the vacuum to the intact skin. The vacuum being distributed to the intact skin by the manifold 110 promotes perfusion by pneumatically pulling the intact skin toward the sleeve 112 for a sustained period of time rather than compressing the tissue site 104 as provided by the current standard of care. Thus, this decompression treatment consists of an initial collapsing of the sleeve 112 that provides a certain amount of splinting at the tissue site 104 followed by a sustained decompression cycle within the chamber 101 the promotes perfusion to heal the sprain. Utilization of the dressing 102 for such decompression treatments significantly reduces the amount of time necessary to heal a sprain compared to the current standard of care.

The standard of care ("SOC") for strains and sprains for many decades has included rest, ice, compression and elevation, also known in the field of practice by the acronym "RICE". This series of treatments is designed to treat the causes of the aforementioned clinical symptoms. Rest takes pressure off of the affected area, allowing the damaged ligament or muscle to repair without additional injury. Ice is normally prescribed to be applied immediately after the injury, 10-20 minutes at a time 3-4 times a day to help reduce swelling and pain due to inflammation. Compression, along with ice, is the main form of treatment that is typically implemented by using elastic material in the form of a wrap or garment. The elastic material applies a positive mechanical force to the affected area to control the swelling. The compression should be applied such that the force being applied reduces in the direction of the heart, which pushes excess fluid up the blood stream in order to be recycled. Elevation of the affected extremity above the heart also helps to minimize the swelling. This form of standard of care is adequate for treating many sprains and strains. After a period of anywhere from 10 days to 24 weeks for minor injuries, patients report a reduction in pain and return to motion. For major injuries, however, patients report a reduction in pain after one year, two years, and even more time. Even after these lengthy time periods, an equally significant number of patients still report pain and no return to motion.

The literature clearly indicates that the healing time for more traumatic sprains and strains is typically much longer ranging from 4 to 6 months. Even then, if the injury is still unstable after this time, surgery is often required to stabilize the ankle. This prolonged healing time represents a significant loss of mobility, and delay in return to functional activity. Even for the majority of sprains and strains, the current standard of care also suffers from several practical drawbacks in addition to inadequate healing. Ice can only applied for a limited time, as prolonged contact is either not practical because it melts or causes even more discomfort and pain because of the cold temperature being applied to the affected extremity. Compression with current devices, especially with elastic wraps, is either inadequate for applying a sufficient and consistent positive force (e.g., the wrap slips over time or is applied and re-applied incorrectly), or actually restricts blood flow and lymph flow. A therapy that can both manage symptoms and accelerate healing is desirable for treating sprains and strains.

The dressing 102 applies the vacuum to the intact skin extending over or surrounding the tissue site 104 that effectively splints and stabilizes the ankle joint of the foot 103, while at the same time provides vacuum or a vacuum to the intact skin which pulls the tissue site 104 outwardly toward the sleeve 112. This pulling force adjacent the intact skin coupled with the immobilization of the joint stimulates the blood flow (perfusion) and lymphatic flow at the tissue site 104 to accelerate healing of the damaged ligament and/or muscle in contrast to current SOC procedures defined by the RICE treatments that only temporarily treat the systems of sprains and strains as such treatments only temporarily reduce inflammation by icing and may actually constrict blood flow and lymph flow by compression. This pulling force allows the damaged tissue to be properly supplied and evacuated with blood flow and lymph flow, thereby promoting perfusion in the subcutaneous portions of the tissue site 104 and reducing edema to accelerate healing. Utilization of the dressing 102 to pull on the intact skin further enhances skin perfusion which significantly reduces the amount of time necessary to heal a sprain compared to the current standard of care.

Thus, the decompression treatment described herein provides the dual advantage of managing pain by reducing swelling and inflammation, but also accelerating healing by increasing blood flow and lymph flow. For example, volunteers with minor sprain injuries have reported a total elimination of pain allowing them to return to ongoing activities after decompression treatments of only three hours. They were able to return to their activities without suffering any pain during or after such activities As indicated above, the current standard of care requires a treatment period of anywhere from 10 days to 24 weeks for minor injuries in order to reduce the pain. Furthermore, the dressing 102 can be comfortably worn by a patient for most of the day to further accelerate healing if desired.

Because the dressing 102 may be light and flexible, wearing the dressing 102 does not restrict patient mobility nearly as much as current compression bandages and the combination ice and compression systems. For example, volunteers with severe ankle sprains who were using a walking boot for several months have reported that the pain relief was the same as using an ice treatment without being confined, and that the decompression treatment allowed them to walk around without pain even without the boot. One volunteer could not place full weight on his ankle without pain, but was able to do so after receiving the decompression treatment. Another volunteer after having a TKA surgery experienced serious swelling even several weeks after surgery. The volunteer elected to use the decompression treatment rather than nice which significantly reduced swelling after one 30 minute therapy treatment per day for four days.

Another volunteer who had a planter fasciitis injury elected to use the decompression therapy that was applied for six hours per day for three days. The volunteer experienced enough pain relief after only three days of therapy, that she was allowed to return to her physical activity. She suffered an earlier knee injury that was severe, and also experienced significant pain relief allowing her to return to her physical activity. Based on all these preliminary results, it is clear that the therapy system 100 offers more significant pain management, accelerates healing efficacy, and facilitates patient mobility and standard of living than does the current standard of care as reported by many volunteers.

As described above, the sleeve 112 may be molded as a single component in a generally tubular shape formed from the sealing material described above that is stretched over the affected extremity and pulled over the manifold 110 to the tissue site 104. In another exemplary embodiment, the sleeve 112 may be formed from an adhesive tape formed from the sealing material described above that is wrapped around the manifold 110. In yet another exemplary embodiment, the sleeve 112 and the manifold 110 may be a composite structure formed as a single piece of material shaped to wrap around a limb to cover the intact skin extending over or surrounding the tissue site 104. In still another exemplary embodiment, the sleeve 112 and the manifold 110 may be a composite structure formed as a single piece of material that is shaped to have a two dimensional profile having a distal portion and a proximal portion including a flexible portion between the distal and proximal portions. The distal and proximal portions may be wrapped around a limb on either side of a joint wherein the flexible portion of the dressing allows articulation of the joint.

Figure 6B:
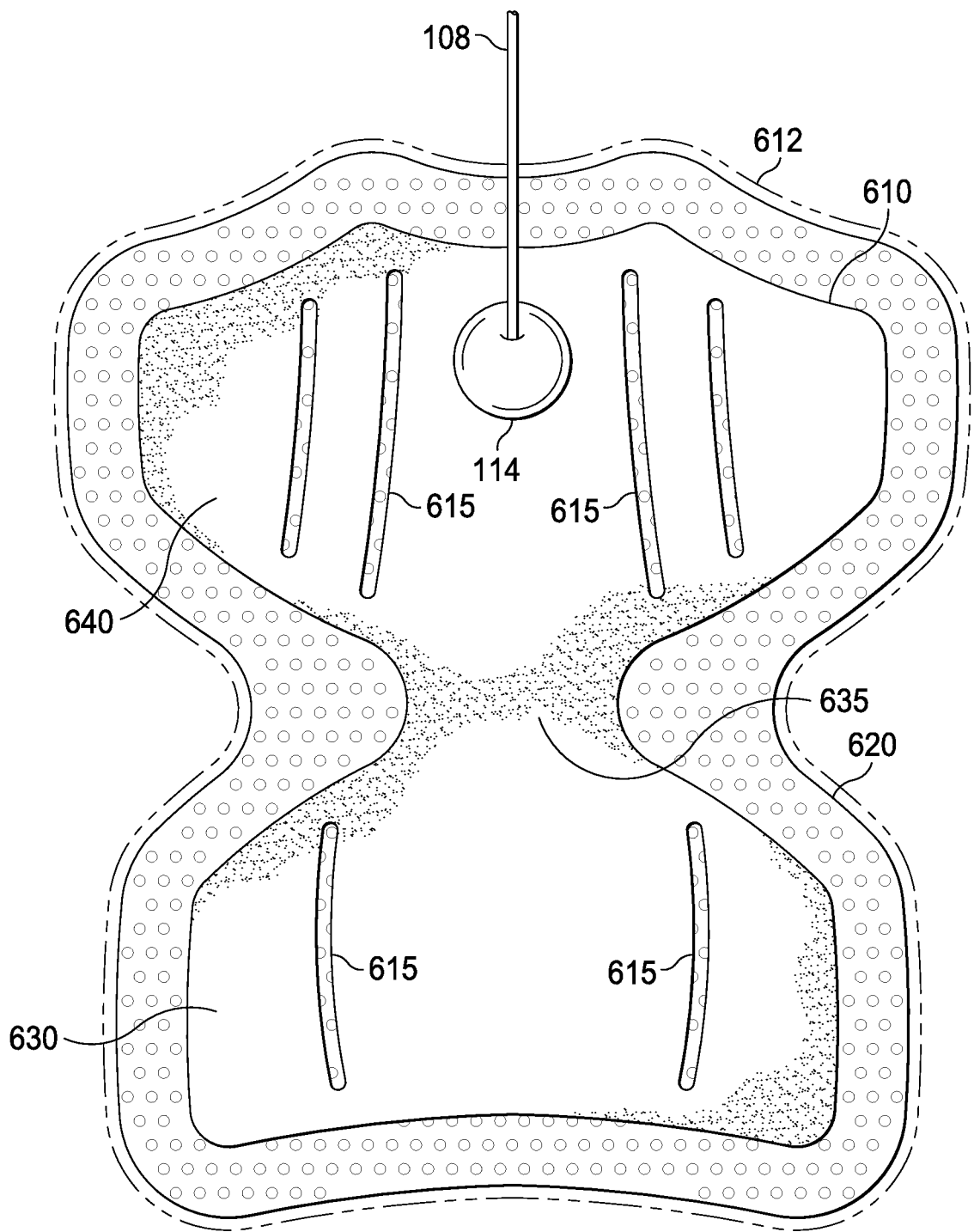
FIG. 6B is a top view of the second exemplary embodiment of the dressing illustrated in FIG. 6A.

Referring now to FIGS. 6A and 6B, a perspective view of a second exemplary embodiment of a dressing 602 is shown for applying vacuum to the intact skin extending or surrounding a tissue site such as, for example, the tissue site 104 on both the distal side and proximal side of the ankle of the foot 103 that allows for articulation of the ankle. The dressing: 602 may operate in substantially the same way as a component of the therapy system 100 as described above and may include components substantially similar to those described above as indicated by the similar numbering scheme preceded by the century number 6. For example, the dressing 602 also forms a chamber 101 with the intact skin extending over and/or surrounding that portion of the tissue site 104 that has been sprained.

The dressing 602 comprises a manifold layer 610 adapted to contact the intact skin surrounding the tissue site 104, and a sleeve layer 612 for enclosing the manifold layer 610 over the intact skin to form the chamber and provide an airtight seal. The dressing 602 further comprises a comfort layer 620 to provide low tack adhesion to the epidermis 103 and an airtight seal. The dressing 602 further comprises a fluid coupling member such as, for example, the connector 114 for fluidly coupling the conduit 108 to the manifold layer 610 through an aperture 611 extending through the sleeve layer 612. The manifold layer 610 may be any breathable material that distributes vacuum uniformly over the intact skin of the tissue site 104 when subjected to a vacuum as described above. The manifold layer 610 may be partially or fully in contact with the intact skin of the tissue site 104. For example, the manifold layer 610 may contact the intact skin extending over the tissue site 104, but not the incision 109 extending through the intact skin at the tissue site 104.

The manifold layer 610 may also have an antimicrobial property as described above to reduce odors generated by the dressing 602. A charcoal filter 613 may be positioned within the connector 114 and adapted to cover the aperture 611 extending through the sleeve layer 612 to further filter odors generated by the dressing 602. Thus, the charcoal filter 613 reduces odors being generated as the chamber of the dressing 602 is being evacuated and after the chamber has been fully evacuated in the decompression mode. The manifold layer 610 may also comprise a series of cutouts or slits 615 to accommodate the contoured shapes of the limb. The slits 615 facilitate the flat, planar manifold layer 610 to war precisely conform to the contoured shapes of the limb.

The comfort layer 620 is disposed adjacent the intact skin to provide additional comfort for the patient and help prevent skin irritation without significantly impeding airflow between the manifold layer 610 and the epidermis 103 as described above. The comfort layer 620 may be produced from a silicone material or from other materials including, for example, hydrocolloids, or hydrogels as may be required for additional beneficial characteristics such as lower costs, better absorption, cooling or moisture donation. Comfort layer 620 may be formed from an occlusive material, and may include a plurality of perforations or holes 621 to allow for the transmittance of negative pressure to the underlying intact skin and to provide for further comfort. The plurality of perforations or holes 621 also allow the sleeve layer 612 to be in partial contact with the epidermis 103 allowing the high tack adhesive to securely anchor the dressing 602 on the limb.

The sleeve layer 612 envelops the manifold layer 610 tightly enough to hold the desired vacuum within the chamber 101 when the dressing 602 is disposed over the intact skin extending over the sprained portion of the tissue site 104 as described above and then wrapped around the limb as necessary to hold the dressing 602 in place. The sleeve layer 612 may be formed from any of the sealing materials described above and may have an acrylic adhesive backing material to seal it over the manifold layer 610. When the sleeve layer 612 includes an adhesive backing material, the slits 615 through the manifold 610 allow the adhesive to contact the intact skin thereby securing the dressing 602 to the limb intermittently to prevent the dressing 602 from slipping and to aid the process of applying the dressing 602 to the limb as illustrated more specifically in FIGS. 7A-7C described below.

Referring more specifically to FIG. 6B, one exemplary embodiment of the dressing 602 may be a composite material or laminate formed by the sleeve layer 612 and the manifold layer 610. The dressing 602 may be shaped to have a two dimensional profile having a distal dressing portion 630 and a proximal dressing portion 640 including a flexible dressing portion 635 between them. The distal dressing portion 630 and proximal dressing portion 640 may be wrapped fully or partially around a limb on either side of an articulating joint so that the flexible dressing portion 635 is positioned at the joint. The flexible dressing portion 635 may have a width narrower than the distal dressing portion 630 and proximal dressing portion 640 to facilitate articulation of the joint while still treating the sprain injury on either side of the joint.

Figure 7A:
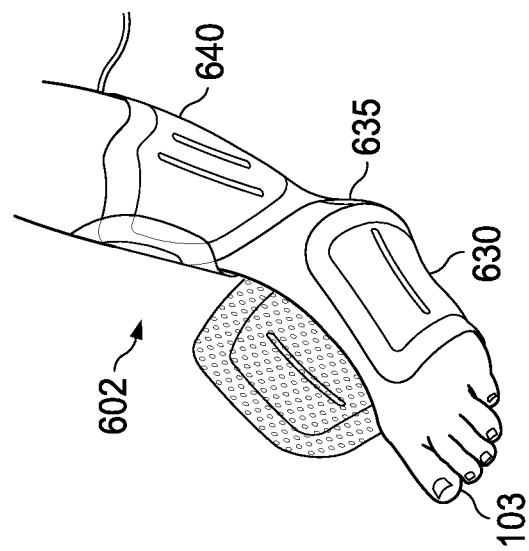
FIGS. 7A-7C are perspective views of the dressing illustrated in FIGS. 6A and 6B showing a heel being placed into the dressing, the dressing being wrapped around the upper ankle above the heel, and the dressing being wrapped around the foot.
Figure 7B:
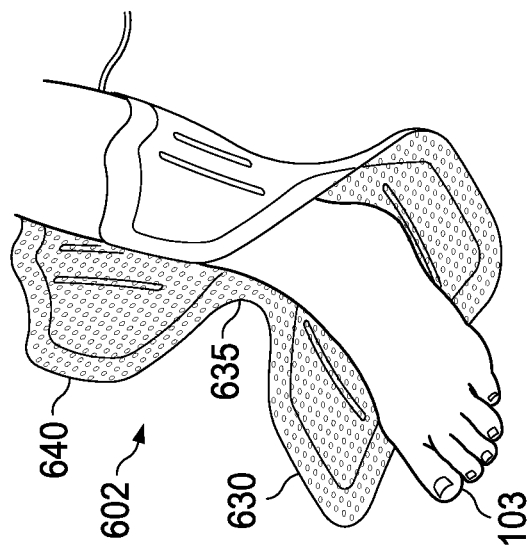
Figure 7C:
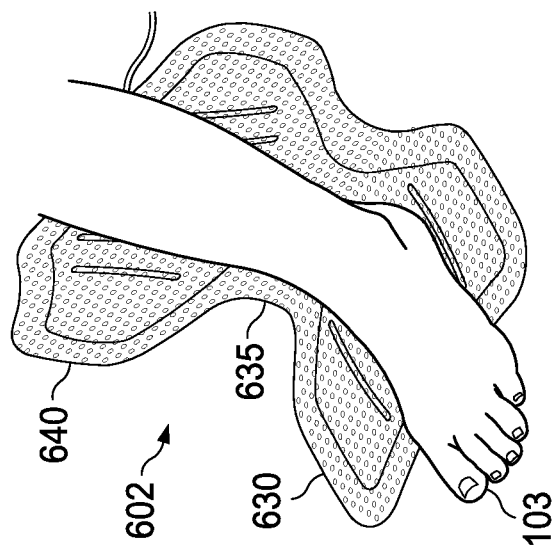

Referring more specifically to FIGS. 7A-7C, an exemplary method for applying the dressing 602 to the tissue site includes, for example, placing the heel of the foot 103 into the flexible dressing portion 635, wrapping the proximal dressing portion 640 around the upper ankle portion of the limb on the proximal side of the ankle joint, and wrapping the distal dressing portion 630 partially around the foot portion of the limb on the distal side of the ankle joint. This embodiment of the dressing 602 facilitates joint articulation and flexing as well as being adjustable for application to the many variants in the anatomy of a limb. It is to be understood that such a two-dimensional embodiment can facilitate joint articulation while at the same time providing bracing or splinting of the limb on either side of the joint as described above. More specifically, the proximal dressing portion 640 may still provide splinting to the upper ankle portion of the limb on the proximal side of the ankle joint, and the distal dressing portion 630 may still provide splinting to the foot portion of the limb on the distal side of the ankle joint. Both features greatly facilitate the rapid healing of sprain injuries while patients may still be ambulatory without being restricted by icing as required by the current standard of care.

Another exemplary embodiment of a method for applying vacuum circumferentially to the intact skin of a tissue site is also disclosed. The method comprises disposing a manifold formed from an open cell, porous material circumferentially around the intact skin of the tissue site, enclosing the manifold within a sleeve formed from a semi-permeable material that seals the manifold within a sealed space between the sleeve and the intact skin, and fluidly coupling the manifold to a vacuum source so that the manifold distributes vacuum to the intact skin of the tissue site.

Although certain illustrative, non-limiting embodiments have been presented, it should be understood that various changes, substitutions, permutations, and alterations can be made without departing from the scope the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, features of any of the embodiments described above may be combined with features of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. An apparatus for applying negative pressure to a tissue site of a patient, the apparatus comprising:
   a manifold having an open cell structure and configured to be circumferentially disposed proximate the tissue site;
   a sleeve configured to cover the manifold and form a chamber containing the manifold to seal the manifold within the chamber between the sleeve and the tissue site;
   a delivery manifold having walls and a divider, the walls and the divider defining a first flow passage and a second flow passage; and
   a delivery tube having a first lumen and a second lumen, wherein the first lumen is fluidly coupled to the first flow passage and the second lumen is fluidly coupled to the second flow passage, wherein the first lumen is bound by a first wall and a second wall, wherein the first wall includes a first protrusion extending toward the second wall and the second wall includes a second protrusion extending toward the first wall, and wherein the first protrusion is configured to touch the second protrusion when a force is applied to the delivery tube;
   wherein the first flow passage, the second flow passage, the first lumen, and the second lumen are configured to receive a negative pressure from a negative-pressure source and deliver negative pressure to the manifold.

2. The apparatus of claim 1, wherein the delivery manifold further includes a plurality of apertures through the walls, wherein the plurality of apertures are configured to fluidly couple the first flow passage and the second flow passage with the manifold.

3. The apparatus of claim 2, wherein the delivery manifold has a length and the plurality of apertures are positioned along the length of the delivery manifold to uniformly direct negative pressure to the manifold.

4. The apparatus of claim 2, wherein the delivery manifold has a length and the diameter of the plurality of apertures varies along the length of the delivery manifold.

5. The apparatus of claim 1, wherein the delivery manifold has a terminal end opposite the delivery tube, and wherein the terminal end of the delivery manifold is open.

6. The apparatus of claim 1, wherein the delivery manifold has a terminal end opposite the delivery tube, and wherein the terminal end of the delivery manifold is capped.

7. The apparatus of claim 1, wherein the first protrusion and the second protrusion are configured to prevent collapse of the first lumen.

8. The apparatus of claim 1, wherein the second lumen is bound by a third wall and a fourth wall.

9. The apparatus of claim 8, wherein the third wall includes a third protrusion extending toward the fourth wall, and the fourth wall includes a fourth protrusion extending toward the third wall.

10. The apparatus of claim 9, wherein the first protrusion and the second protrusion are configured to prevent collapse of the first lumen and the third protrusion and the fourth protrusion are configured to prevent collapse of the second lumen.

11. The apparatus of claim 1, wherein the delivery manifold has a rectangular cross-section.

12. The apparatus of claim 1, wherein the delivery tube has an elliptical cross-section.

13. The apparatus of claim 1, wherein the delivery manifold and the delivery tube are coupled by a transition region.

14. The apparatus of claim 1, wherein the delivery manifold and the delivery tube are formed from a flexible material.

15. The apparatus of claim 1, wherein the delivery manifold is further configured to receive temperature-controlled airflow from a source of positive pressure and deliver the temperature-controlled airflow to the manifold.

16. The apparatus of claim 1, further comprising a substantially rigid case enclosing the sleeve.

17. The apparatus of claim 1, further comprising a flexible walking boot enclosing the sleeve.

18. An apparatus for applying negative pressure to a tissue site of a patient, the apparatus comprising:
    a manifold having an open cell structure and configured to be circumferentially disposed proximate the tissue site;
    a sleeve configured to cover the manifold and form a chamber containing the manifold to seal the manifold within the chamber between the sleeve and the tissue site;
    a delivery manifold having:
       walls and a divider, the walls and the divider defining a first flow passage and a second flow passage;
       a plurality of apertures through the walls, wherein the plurality of apertures are configured to fluidly couple the first flow passage and the second flow passage with the manifold; and
       a length, wherein the diameter of the plurality of apertures varies along the length of the delivery manifold; and
    a delivery tube having a first lumen and a second lumen, wherein the first lumen is fluidly coupled to the first flow passage and the second lumen is fluidly coupled to the second flow passage;
    wherein the first flow passage, the second flow passage, the first lumen, and the second lumen are configured to receive a negative pressure from a negative-pressure source and deliver negative pressure to the manifold.

19. The apparatus of claim 18, wherein the first lumen is bound by a first wall and a second wall.

20. The apparatus of claim 19, wherein the first wall includes a first protrusion extending toward the second wall, wherein the first protrusion is configured to prevent the first wall from touching the second wall when a force is applied to the delivery tube.

21. The apparatus of claim 19, wherein the second wall includes a second protrusion extending toward the first wall, wherein the second protrusion is configured to prevent the second wall from touching the first wall when a force is applied to the delivery tube.

22. An apparatus for applying negative pressure to a tissue site of a patient, the apparatus comprising:
    a manifold having an open cell structure and configured to be circumferentially disposed proximate the tissue site;

a sleeve configured to cover the manifold and form a chamber containing the manifold to seal the manifold within the chamber between the sleeve and the tissue site;

a delivery manifold having walls and a divider, the walls and the divider defining a first flow passage and a second flow passage; and a delivery tube having a first lumen and a second lumen, wherein the first lumen is fluidly coupled to the first flow passage and the second lumen is fluidly coupled to the second flow passage;

wherein the first flow passage, the second flow passage, the first lumen, and the second lumen are configured to receive a negative pressure from a negative-pressure source and deliver negative pressure to the manifold; and wherein the delivery manifold has a terminal end opposite the delivery tube, and wherein the terminal end of the delivery manifold is capped.

\* \* \* \* \*